(12) United States Patent
Katarow et al.

(10) Patent No.: US 6,731,962 B1
(45) Date of Patent: May 4, 2004

(54) FINGER OXIMETER WITH REMOTE TELECOMMUNICATIONS CAPABILITIES AND SYSTEM THEREFOR

(75) Inventors: Frank Katarow, Pewaukee, WI (US); Eugene Palatnik, Pewaukee, WI (US)

(73) Assignee: Smiths Medical PM, Inc., Waukesha, WI (US)

( * ) Notice: Subject to any disclaimer, the term of this patent is extended or adjusted under 35 U.S.C. 154(b) by 0 days.

(21) Appl. No.: 10/284,239

(22) Filed: Oct. 31, 2002

(51) Int. Cl.[7] .................................................. A61B 5/00
(52) U.S. Cl. ....................................... 600/323; 128/903
(58) Field of Search ................................. 600/310, 322, 600/323, 346; 128/903

(56) References Cited

U.S. PATENT DOCUMENTS

| | | | |
|---|---|---|---|
| 5,490,523 A | * | 2/1996 | Isaacson et al. ............. 600/323 |
| 5,830,137 A | * | 11/1998 | Scharf .......................... 600/323 |

* cited by examiner

*Primary Examiner*—Eric F. Winakur
(74) *Attorney, Agent, or Firm*—Louis Woo

(57) ABSTRACT

A finger oximeter has fitted thereto a RF transmitter circuit so that the measured $SpO_2$, and other physical parameters from a patient, may be transmitted telecommunicatively to a monitor device remotely located from the finger oximeter. The RF transmitter circuit is mounted on a PC board that is provided in the housing of the finger oximeter, and works in cooperation with the oximetry circuit that is also mounted on a PC board in the housing of the finger oximeter. The two PC boards may be combined as one. To receive the RF signal, a RF receiver is provided to the remote monitor device, which also includes a processing circuit for processing the incoming RF signal, and a converter circuit for converting the processed digital signal into an analog signal for display at the remote monitor device. In place of a one-way RF link, the finger oximeter may be equipped with a RF transceiver circuit that is capable of transmitting as well as receiving RF signals from the remote monitor device, which likewise is fitted with a RF transceiver circuit. The finger oximeter could be activated by the patient manually, by means of a switch provided at the housing, or remotely by means of a signal provided from the remote monitor device. The finger oximeter may or may not include a display.

28 Claims, 6 Drawing Sheets

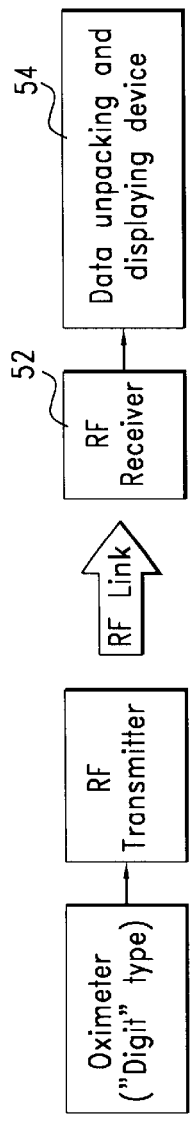
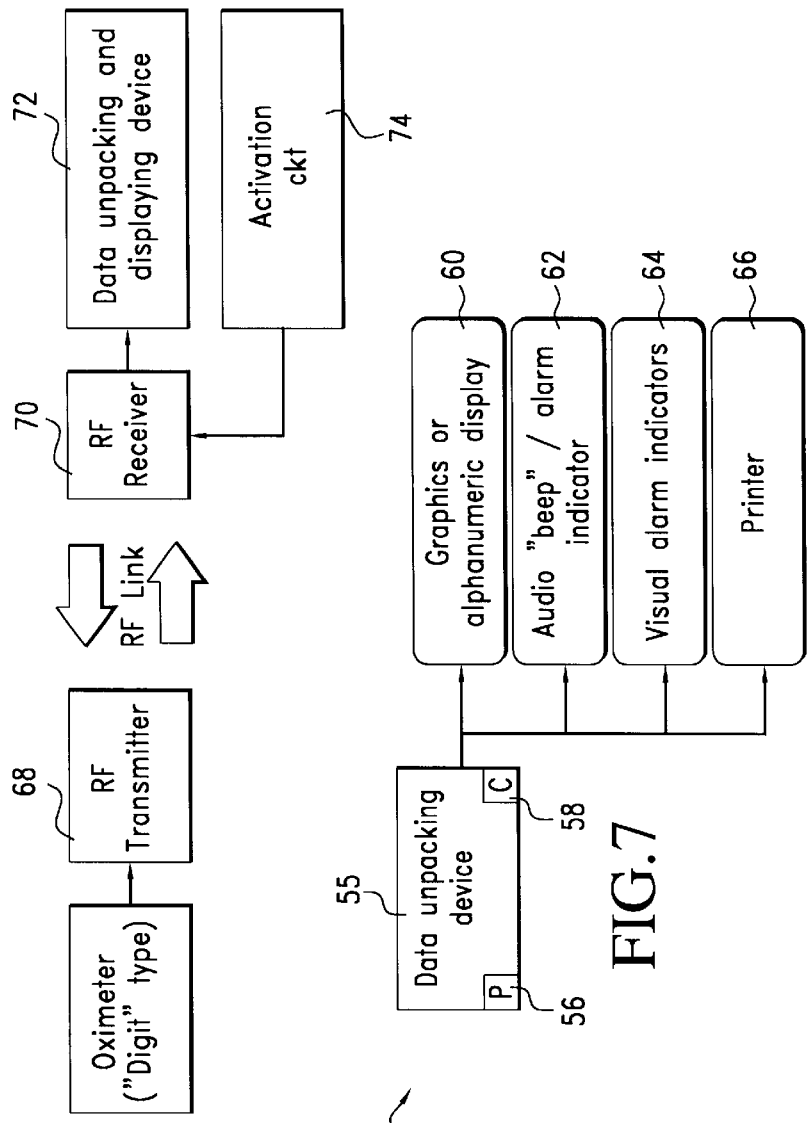
FIG.6
FIG.8
FIG.7

FINGER OXIMETER WITH REMOTE TELECOMMUNICATIONS CAPABILITIES AND SYSTEM THEREFOR

FIELD OF THE INVENTION

The present invention relates to finger oximeters and more particularly to a finger oximeter with remote telecommunications capabilities and a system for monitoring the signals from such finger oximeter.

SUMMARY OF THE INVENTION

In co-pending U.S. application Ser. No. 09/940,418, assigned to the same assignee as the instant application, a finger oximeter with a unique finger grip suspension system is disclosed. The disclosed finger oximeter is a standalone device. The finger oximeter of the instant invention improves on the standalone finger oximeter of the co-pending application by providing it with telecommunications capabilities that enable it to transmit data acquired from a patient to a remote device, such as a monitor device, that allows remote monitoring of a patient.

In addition to the oximetry circuitry that controls the operation of the radiation emitter that outputs a multi-frequency light to the finger and the sensor for sensing the radiation passing the finger for obtaining data from the patient and then calculating the oxygen saturation level of blood from the acquired data, the present invention oximeter further includes a transmission circuit that may be a radio frequency RF circuit that works in cooperation with the finger oximetry circuit so that a signal such as for example a RF signal that contains the calculated oxygen saturation level of blood of the patient may be transmitted to a remote device. The RF circuit is provided on a PC circuit board that is mounted to the housing of the finger oximeter, along with a circuit board to which the finger oximetry circuit and other circuits such as the power circuit and processor circuit are mounted. Instead of separate printed circuit boards, a single circuit board that contains all of the circuitries of the RF transmitter equipped oximeter of the instant invention may be mounted completely within the housing of the finger oximeter.

The present invention finger oximeter therefore includes a housing having an opening through which a finger of a patient may be placed, a radiation emitter provided in the housing for outputting a multifrequency radiation to the finger, a sensor provided in the housing for detecting the radiation from the emitter that passes though, or reflects from, the finger of the patient so that data relating to the physical attributes of the patient may be acquired, at least one circuit provided in the housing for operating the radiation emitter and the sensor, and to calculate from the data acquired at least the oxygen saturation level of blood of the patient, and another circuit provided in the housing that transmits as a RF signal the calculated oxygen saturation of blood of the patient to a remote site.

The instant invention also relates to the system in which the RF signal transmitted by the finger oximeter is received by a remote device, such as for example the Vital Signs Monitor being sold by the assignee which has incorporated therein a RF receiver attuned to receive the RF signal transmitted from the finger oximeter. The remote device may be equipped with a transceiver that allows the observer at the remote monitor device to control the operation of the finger oximeter. This is done by the observer at the remote monitoring system activating a switch that sends out a signal that can activate/deactivate the remote finger oximeter.

The RF signal sent by the finger oximeter may be sent in the form of data packets. A depacking component which may include a processing circuit and a converter circuit is provided at the remote monitor device for unpacking the data packets and converting the unpacked data from digital to analog so that the physical attributes of the patient being monitored may be shown on the display of the monitor device. The transmission of the RF signal, and the control of the finger oximeter by the remote monitor device, may be effected by a telecommunications protocol such as for example Bluetooth.

BRIEF DESCRIPTION OF THE FIGURES

The instant invention will become apparent and will be best understood by reference to the following description of an embodiment of the invention taken in conjunction with the accompanying drawings, wherein:

FIG. 6 is block diagram illustrating the transmission of a RF signal from the finger oximeter of the instant invention to a remote monitor device;

FIG. 7 shows the various components of the remote monitor device of the system of the instant invention; and FIG. 8. is a block diagram illustrating the interaction of the finger oximeter and the remote monitor device equipped to control the operation of the finger oximeter of the instant invention.

DETAILED DESCRIPTION OF THE INVENTION

FIGS. 1a–1d illustrate the housing of a finger oximeter that is disclosed in the aforenoted co-pending application 09/940,418, the disclosure of which being incorporated by reference herein. The housing of the finger oximeter of the instant invention may have the same housing as that of the '418 application. Accordingly, finger oximeter 2, as shown in the plan view of FIG. 1a, has a display 4 that enables the finger oximeter to display the various physical attributes of a patient including for example the oxygen saturation level of blood ($SpO_2$) and the heart rate of the patient.

Figure 1B:
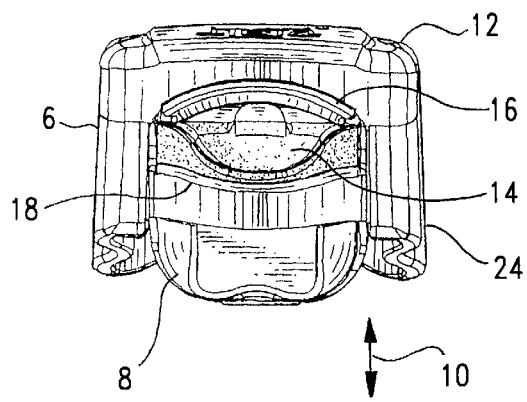
FIGS. 1a–1d are different views of a finger oximeter, particularly the housing thereof, of the instant invention.
Figure 1A:
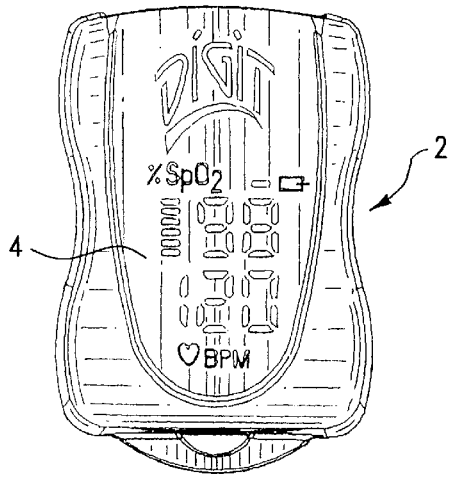
Figure 5:
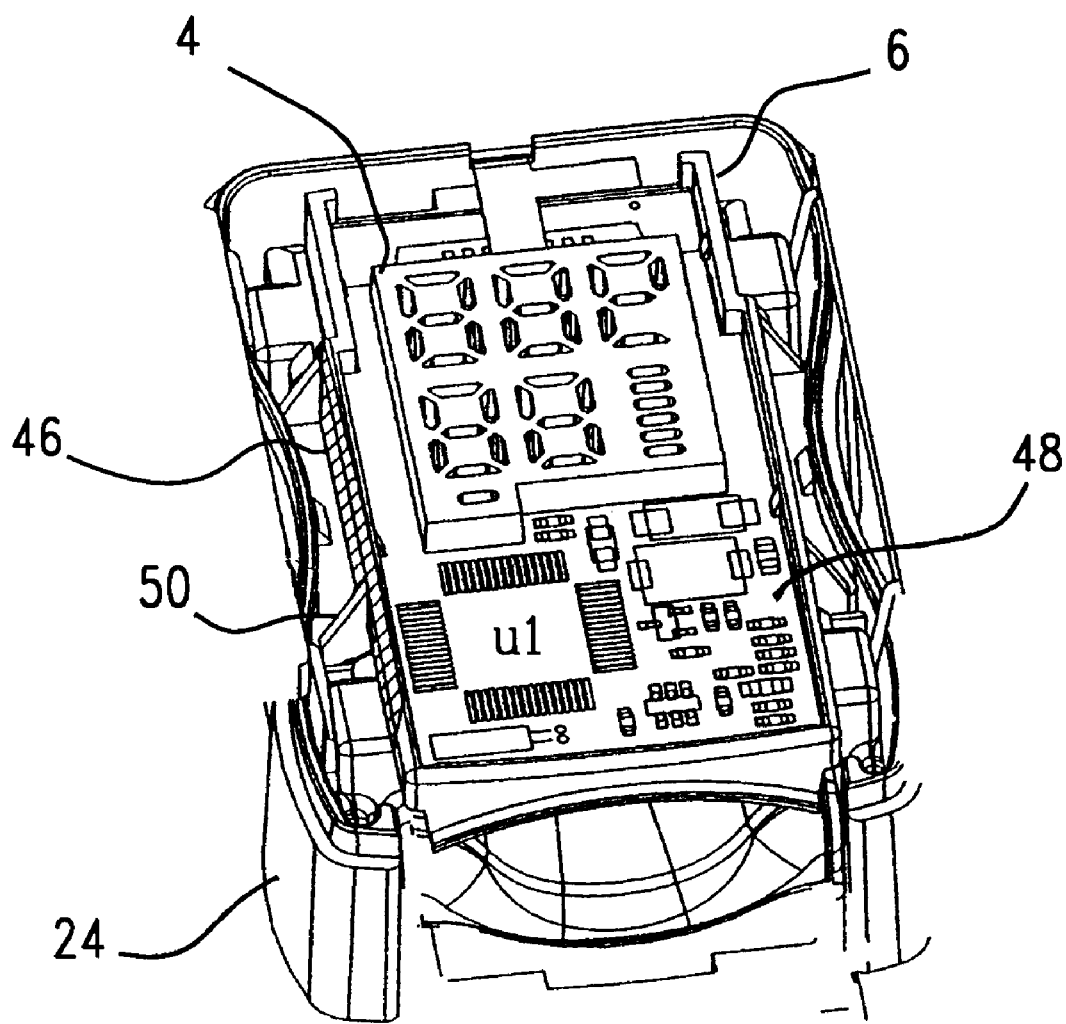
FIG. 5 is a perspective view of the upper half of the housing of the instant invention, with the cover removed, that shows the mounting of the circuitries of the instant invention finger oximeter.

As shown in the front view of FIG. 1b, finger oximeter 2 is made up of two housing portions 6 and 8, with the lower housing 8 movable relative to the upper housing 6 vertically as shown by directional arrow 10. Upper housing 6 is protected by a cover 12. Mounted in upper housing portion 6 and protected by cover 12 are the display and circuit boards as shown in FIG. 5. An opening 14 is formed between upper and lower housing portions 6 and 8. Each of the finger portions 6 and 8 is fitted with a finger pad that together form a contour for gripping a finger that is placed into or positioned in opening 14. The respective finger pads mounted to the upper housing portion 6 and the lower housing portion 8 are designated 16 and 18, respectively. By a plurality of springs, not shown, upper housing portion 6 and lower housing portion 8 are vertically biased towards each other so as to securely grip a finger positioned between them into opening 14. The system for gripping a finger placed between upper housing portion 6 and lower housing portion 8 of the finger oximeter 2 is given in detail in the aforenoted '418 application.

With the finger oximeter of the '418 application, in order to read the oxygen concentration of blood of the patient, a nurse or doctor has to be near the patient so that she can read the display mounted to the finger oximeter. This is fine only if a single reading at a given point of time is needed. However, for those instances where a continuous monitoring of the patient's physical attributes including the $SpO_2$, is needed, and where the medical practitioner could not possibly be in close proximity of the patient at all times, remote monitoring of the data being collected from the patient is desired.

Figure 1D:
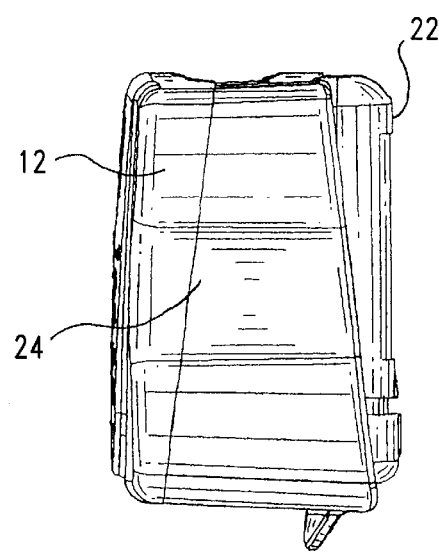
Figure 1C:
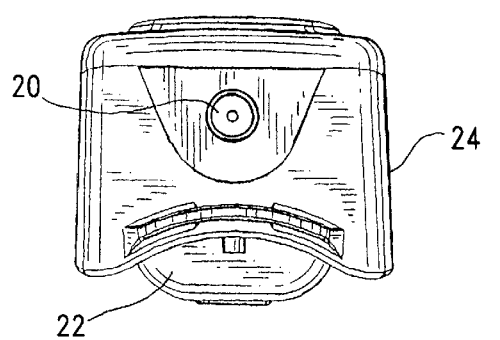

As shown in FIG. 1c, finger oximeter 2 has a backside that has mounted thereto a switch 20, which enables a user to manually activate the device, i.e. by energizing the various circuits of the printed circuit board(s) mounted in the housing of the finger oximeter. The battery module required for energizing the various components and mounted to the lower portion of housing portion 8 is designated 22. Although shown with a switch 20 and a display 4, the finger oximeter of the instant invention may actually be configured not to include any display 4, or switch 20, if it is determined that the operation of the finger oximeter and the monitoring of the data acquired from the patient from the finger oximeter should be done remotely from the finger oximeter and, of course, the patient to which the finger oximeter is fitted.

FIG. 1d is a side view of the finger oximeter which shows cover 12 attached to a casing 24.

Figure 2:
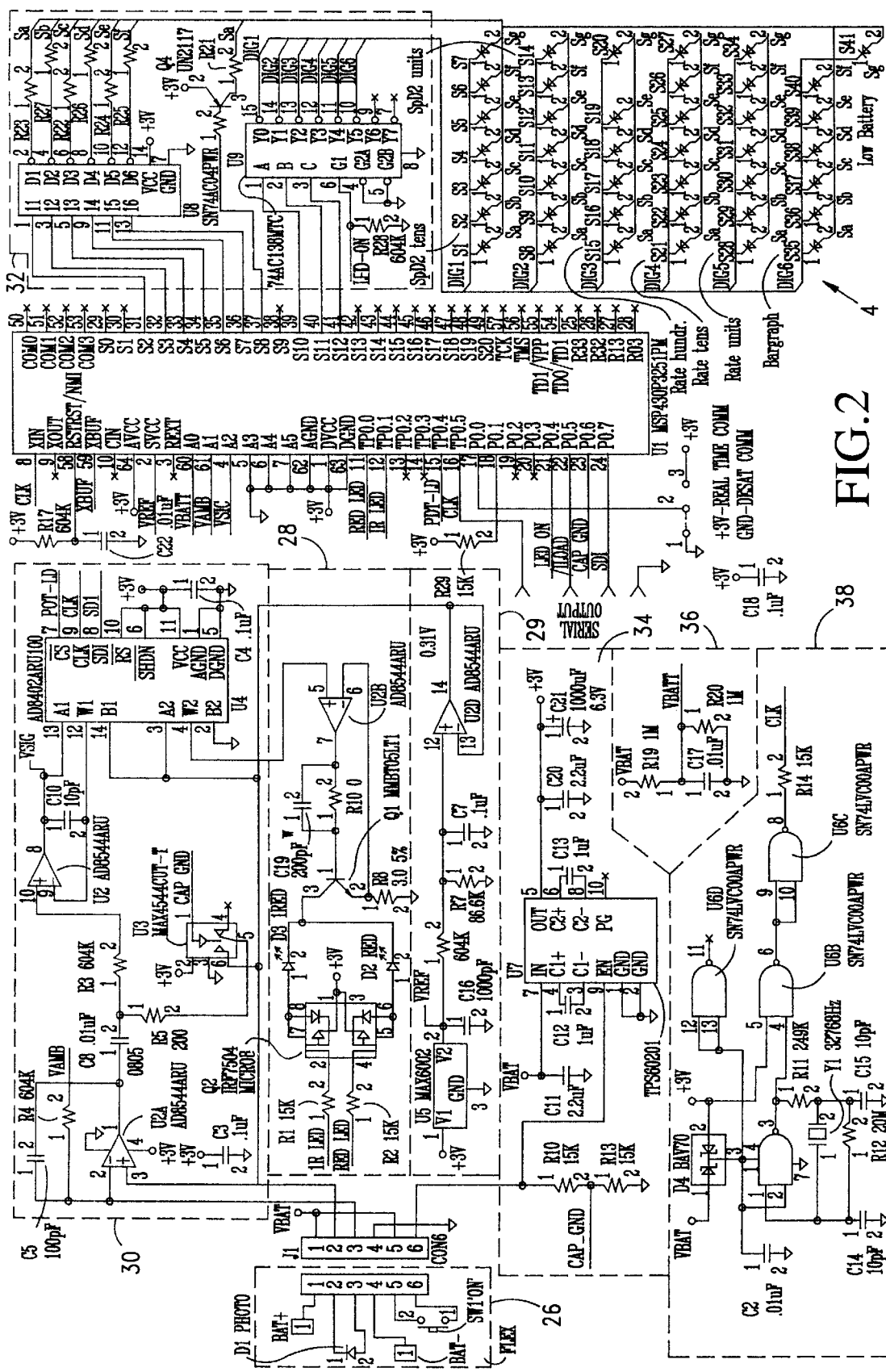
FIG. 2 is the finger oximetry circuit for the operation of the finger oximeter of FIG. 1.

The schematic of the oximetry circuit of the finger oximeter is shown in FIG. 2. For ease of discussion, the various major functions of the circuit are separately grouped together as functional circuits by dotted lines.

The photodetector (D1) is provided in the housing, more specifically in lower housing portion 8 of the embodiment of the finger oximeter of the instant invention as shown in FIGS. 1a–1d. Switch 20, designated SW1 in FIG. 2, is also provided on flexible strip 26 fitted to the lower housing portion, or the lower finger grip 18, of the finger oximeter of the instant invention. When pushed on, power is provided to a radiation emitter, made up of LEDs having different frequencies that are a part of functional circuit 28. The multi-frequency light from the LEDs, in the form of radiation, is directed to the finger placed between the upper and lower finger grip portions 6 and 8 of the finger oximeter. Once the finger is removed from opening 16 and therefore away from the upper and lower grip portion 6 and 8, microprocessor U1 would turn off the device after a predetermined time period, for example 8 seconds, to conserve energy.

The flexible strip 26 is connected to a functional circuit 30 by a conventional coupling. Functional circuit 30 is the analog detector preconditioning circuit that measures the input electrical current signal from the finger of the patient, where the analog current signal is converted to an analog voltage signal. The analog voltage signal is amplified by an op amp U2C, which outputs an amplified analog voltage signal VSIG. The dynamic range of the signal is controlled by IC circuit U4, which acts as an integrated digital potentiometer.

The amplified analog voltage signal VSIG is input to microprocessor U1 at input A2. The analog voltage signal is converted by processor U1 to a corresponding digital signal and output to functional circuit 32, which is a LED driver circuit comprising driver IC circuits U8 and U9. The driver circuit 32 provides the signal to the various digits DIG 1 to DIG 6 for displaying the information collected from the patient on display 4. If no display is provided on the finger oximeter of the instant invention, then functional circuit 32 and the LED display 4 may be removed from the circuit. On the other hand, both display 4 and functional circuit 32 may be provided on the finger oximeter of the instant invention even if the measured physical attributes of the patient may be displayed remotely from the finger oximeter, so that both the patient as well as the medical practitioner may monitor the patient data.

Another functional circuit illustrated in FIG. 2 is function circuit 28, which is a variable LED driver circuit that drives the two LEDs that emit the multi-frequency light directed to the finger of the patient through apertures provided in the upper half 6 of the finger oximeter. The apertures provided in the upper and lower portions 6, 8 of the housing, as well as the finger pads 16, 18, enable the multi-frequency light from the LEDs of the light emitter to be directed to the finger, and the defused light through the finger of the patient being sensed by the photodetector D1. The resulting current signal sensed by detector D1 is provided to the analog detector pre-conditioning circuit 30.

Functional circuit 34 is a switching power supply circuit that regulates the power to be supplied to the various components of the FIG. 2 oximetry circuitry. Functional circuit 36 is a battery voltage divider circuit that identifies whether the voltage from the battery pack 22 is low.

Functional circuit 38 is a timing circuit for the components of the finger oximeter. A clock pulse is generated from circuit 38 for microprocessor U1 by component U6A. Components U6B and U6C in combination ensure that there is enough voltage from battery pack 22 if the voltage output is less than three volts so that the appropriate clocking signals are provided for the various components of the finger oximetry circuit of FIG. 2.

Figure 3:
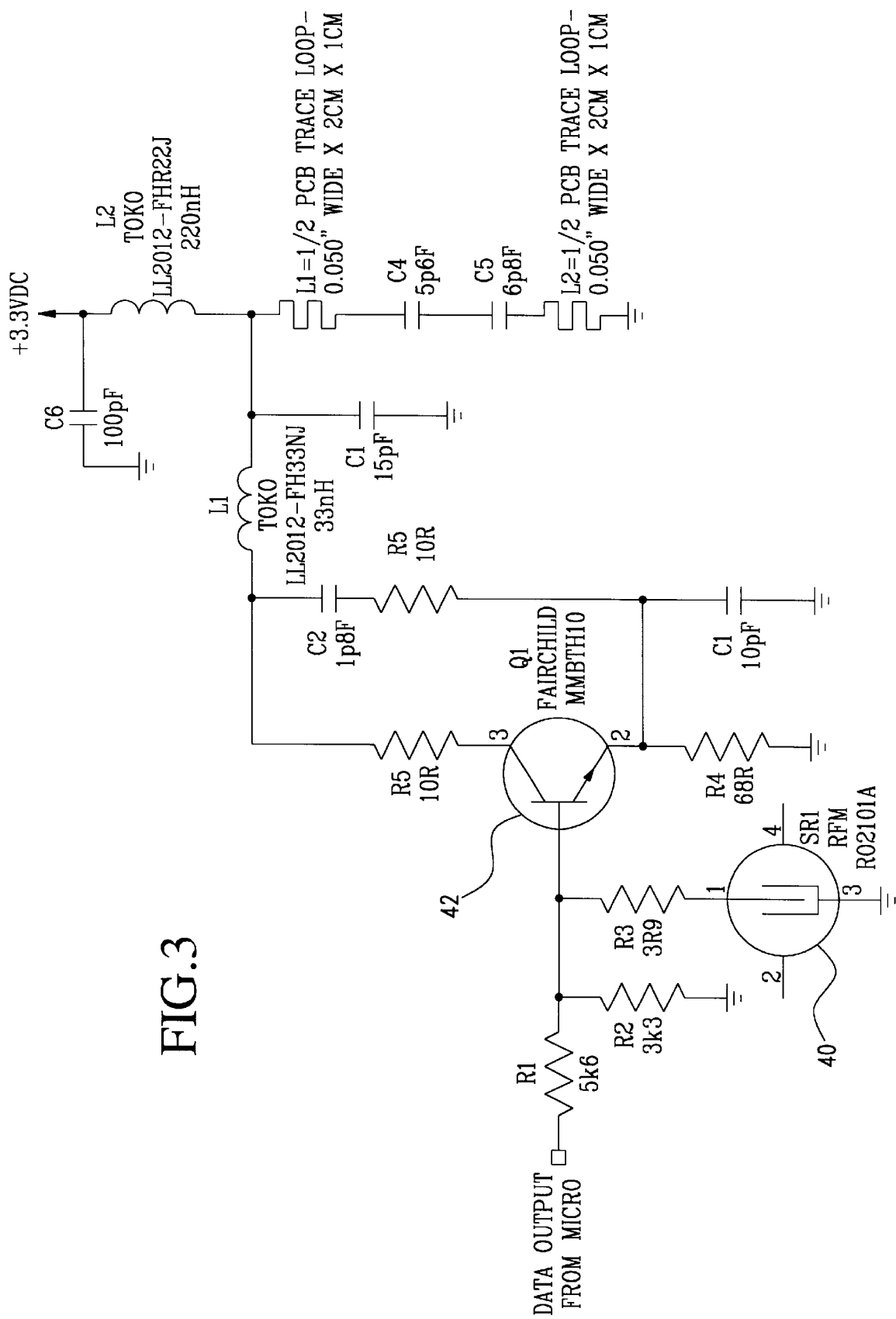
FIG. 3 is a transmission circuit that works in cooperation with the oximetry circuit of FIG. 2 for transmitting the measured physical attributes of the patient to a remote location.

FIG. 3 is a schematic of the RF transmitting circuit of the finger oximeter of the instant invention. In addition to ground, the RF transmitter circuit of FIG. 3 has an input, identified as DATA, that is connected to the SDI output, i.e., pin 24 of microprocessor U1 as shown in the FIG. 2 circuit. The FIG. 3 circuit is moreover connected to the FIG. 2 circuit by means of its input power of +3.3 VDC, which is connected to the output from capacitor C21 of functional circuit 34 of the FIG. 2 oximetry circuit. For the FIG. 3 circuit, component 40, which is a SAW ceramic resonator, defines the frequency of the RF signal to be output by the FIG. 3 circuit. The frequency is selectable by the user for the transmitter circuit, and be attuned to the receiver circuit of the remote monitor device. Transistor Q1, designated 42, acts as both an amplifier and an oscillator, together with components C2, L1 and C3, for outputting the RF signal to the antenna of the transmitter circuit, which is represented by the loop of inductors L1, L2 and capacitors C4, C5. The power for the circuit is provided by the 3.3 VDC.

Figure 4:
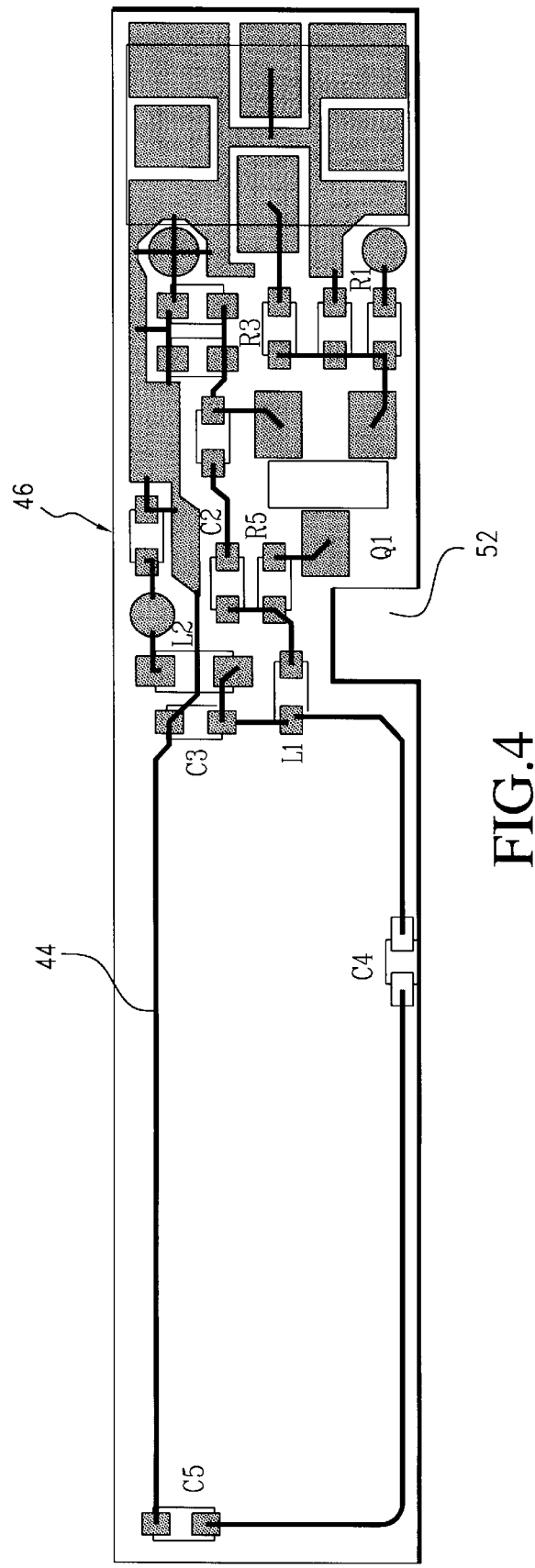
FIG. 4 illustrates the printed circuit board (PCB) onto which the circuit of FIG. 3 is mounted.

The looped antenna 44 is best shown in the printed circuit board 46 of FIG. 4. Note that the various components are etched and mounted to circuit board 46 of FIG. 4.

As best shown in FIG. 5, with cover 12 removed, the upper portion 6 of housing 2 of the finger oximeter is shown to include display 4 and a printed circuit board 48 upon which most of the various components of the oximetry circuit of FIG. 2 are mounted. Also mounted to the side of circuit board 48 is circuit board 46 which has the RF transmitter circuit thereon. Circuit board 46 is shown to be attached to the sidewall of upper portion 6 and is fitted and held thereto by a shoulder 50 that mates with a slot 52 (FIG. 4) notched to printed circuit board 46.

The system to which the finger oximeter of the instant invention is part of is illustrated in FIG. 6. As shown, the patient data, once collected by the oximetry circuit, is forwarded to the RF transmitter. There, an RF signal is sent by means of a RF link to a remote monitor device, for example a Vital Signs monitor being sold by the assignee. To enable it to receive the RF signal from the RF transmitter, a RF receiver 52 is built into the remote monitor device. The device further includes a data unpacking and displaying device 54. Upon receipt of the RF signal, RF receiver 52 sends the signal to device 54, which may include a processing unit/circuit and a converter unit/circuit. The processing circuit processes the received RF signal, which may be sent in the form of data packets. The data packets are unpacked or processed by the processing circuit and converted by the converter circuit from digital to analog. The analog signal could then be displayed on the monitor of the remote monitoring device.

The data unpacking device 54 is further shown in FIG. 7, which shows the device to include a processing unit 56 and a converter unit 58. When converted from digital to analog, the analog signals are displayed either as graphics or alphanumeric data per the display 60. The unpacked signal could also be provided as an audio alarm per an alarm indicator 62 provided at the remote monitor device. Visual alarm indicators 64 may also be provided at the remote monitor device to provide visual alarms to the nurse or user, if a certain undesirable threshold of the being measured physical attribute of the patient is reached or exceeded. A printer 66 may also be provided to the remote monitor device for the purpose of printing out a copy of the $SpO_2$, or other attributes of the patient being monitored.

FIG. 8 illustrates an embodiment of the instant invention in which bidirectional transmission takes place between the finger oximeter and the remote monitor device. In this instance, instead of an RF transmitter circuit, the finger oximeter is equipped with a RF transceiver circuit 68 that enables the oximeter to transmit its oximetry signals to the RF transceiver circuit 70 of the remote monitor device by the bidirectional RF link. The RF devices 68, 70 of the FIG. 8 embodiment is adaptable to operate in a Bluetooth protocol so that signals may be transmitted bidirectionally between the finger oximeter and the remote monitor device. As discussed per the FIG. 6 system, the RF signal received from RF transceiver 68 is unpacked and converted by the data unpacking and displaying device 72 so that the being monitored blood oxygen saturation of the patient is displayed at the remote monitor device.

In addition to the remote monitoring of the patient, the remote monitor device of the system of FIG. 8 has an activation circuit 74 that enables the user of the remote monitor device to activate/deactivate the finger oximeter being worn by the patient. This is desirable in those instances where the patient has to wear the finger oximeter for an extended period of time, and for the conservation of energy for the finger oximeter. Thus, a signal may be sent out by the activation circuit 74 to either activate the finger oximeter or deactivate it.

As noted above, even though the finger oximeter illustrated in FIGS. 1a–1d does include a display that displays to the patient the being measured $SpO_2$ and other physical parameters, and a switch to allow the user to manually turn the device on, it should be appreciated that the display on the finger oximeter may be omitted insofar as the remote monitoring of the patient's physical parameters at a remote location means that readings at the finger oximeter may not be necessary. So, too, by being able to remotely control the activation of the finger oximeter, the switch provided for the finger oximeter as shown in FIGS. 1a–1d may not be necessary. Also, by being able to deactivate the finger oximeter remotely so as to overcome the automatic deactivation of the finger oximeter (provided that the finger is removed from the finger oximeter) if it is not being used for a period of time, the energy of the battery pack for the finger oximeter is conserved.

What is claimed is:

1. An oximeter, comprising:
   a housing having an opening through which a finger of a patient is positioned;
   a radiation emitter provided in said housing for outputting a multi-frequency radiation to said finger;
   a sensor provided in said housing for detecting the radiation from said emitter passing said finger so as to acquire data relating to the physical attributes of said patient;
   at least one circuit provided in said housing for effecting the respective operations of said radiation emitter and said sensor, and to calculate from the data acquired from said sensor at least the oxygen saturation level of blood of said patient; and
   at least an other circuit provided in said housing for establishing a bidirectional RF link between said oximeter and a remote device separate from said housing, said other circuit working cooperatively with said one circuit for transmitting a RF signal representing the calculated blood saturation level of said patient to said remote device.

2. Oximeter of claim 1, wherein said other circuit comprises a RF transmitter circuit on a circuit board mounted within said housing for transmitting said signal via said RF link to a remote RF receiver of said remote device.

3. Oximeter of claim 1, wherein said housing comprises two halves one of which has fitted thereto one circuit board whereon said one circuit is mounted and another circuit board whereon said other circuit is mounted.

4. Oximeter of claim 1, further comprising:
   a display at said housing for displaying the oxygen saturation of blood of the patient; and
   a switch at said housing not responsive to the placement of said finger in said housing for enabling a user to selectively activate said oximeter.

5. Oximeter of claim 2, wherein said RF transmitter circuit can transmit the signal at a selectable frequency.

6. Oximeter of claim 1, wherein said RF signal is sent via Bluetooth protocol.

7. Oximeter of claim 1, further comprising:
   an energy source provided in said housing; and
   a power circuit for supplying power from said energy source to said radiation emitter, said sensor, and said first and second circuits, said power circuit may be activated or shut down by the activation of a switch not responsive to the placement of said finger in said housing located at said housing or by a signal transmitted from said remote device.

8. An oximeter, comprising:
   a housing having an opening through which a finger of a patient is positioned;

a radiation emitter provided in said housing for outputting a multi-frequency radiation to said finger;

a sensor provided in said housing for detecting the radiation from said emitter passing said finger so as to acquire data relating to the physical attributes of said patient;

at least one circuit provided in said housing for effecting the respective operations of said radiation emitter and said sensor, and to calculate from the data acquired from said sensor at least the oxygen saturation level of blood of said patient;

at least an other circuit provided in said housing working cooperatively with said one circuit for transmitting a RF signal representing the calculated blood saturation level to a remote device; and a processor circuit for controlling the respective operations of said radiation emitter, said sensor, and said first and second circuits, the operation of said processor circuit may be controlled by a signal transmitted from said remote device.

9. In combination, a housing having an opening through which a finger of a patient is positioned, a light emitter provided in said housing for radiating the finger with a multi-frequency light, a photo sensor provided in said housing for sensing the light passing through the finger, a first circuit provided in said housing for converting the sensed light to data representing physical attributes of the patient including $SpO_2$, a second circuit working in cooperation with said first circuit for establishing a bidirectional telecommunications link with and transmitting the data in packet format to a remote device unattached to said housing having a display, said remote device having a transceiver circuit attuned to receive data packets from said second circuit, the data packets being converted by a processing circuit in said remote device and displayed as the $SpO_2$ of the patient at said remote device.

10. Combination of claim 9, wherein said second circuit comprises a RF transceiver circuit and wherein said transceiver circuit comprises another RF transceiver circuit, both said RF transceiver circuits being selected to operate at a given frequency.

11. Combination of claim 9, wherein said signal processing circuit unpacks the data packets from said second circuit, said remote device comprises a display driver circuit for displaying the unpacked data as the $SPO_2$ on said remote device.

12. Combination of claim 9, wherein said housing comprises a display whereon the $SPO_2$ of the patient can be displayed, so that the $SPO_2$ of the patient could be displayed at both said housing and said remote device.

13. Combination of claim 9, wherein said housing comprises two halves biased toward each other, respective circuit boards having mounted thereon said first and second circuits fitted in one of said halves, a switch provided to said housing not responsive to the placement of the finger of said patient in said housing to enable manual activation of said light emitter, photo sensor, and said first and second circuits.

14. Combination of claim 9, further comprising:

a power circuit for supplying power to said light emitter, said photo sensor, and said first and second circuits, said power circuit may be activated or shut down by the activation of a switch located at said housing not responsive to the placement of the finger of said patient in said housing or by a signal transmitted from said remote device.

15. A system for remotely determining the blood oxygen level in the blood of a patient, comprising:

an oximeter having
a housing with an opening through which a finger of a patient is positioned;
a radiation emitter provided in said housing for radiating said finger with a multi-frequency radiation;
a sensor provided in said housing for acquiring data from the radiation passing said finger;
a processor circuit provided in said housing for operating said radiation emitter and said sensor, and for calculating from the data acquired by said sensor at least the oxygen saturation level of blood of said patient; and
a transceiver circuit provided in said housing for telecommunicatively transmitting the calculated blood saturation level from said housing; and a monitor device remote and separate from said oximeter having
an other transceiver circuit for establishing a bidirectional telecommunication link with said oximeter for receiving the calculated blood saturation level from said oximeter; and
a display for displaying the received blood saturation level.

16. System of claim 15, wherein said transceiver circuit of said oximeter comprises a RF transmitter circuit, the calculated blood saturation level being transmitted by said RF transmitter circuit as a RF signal; and wherein said other transceiver circuit comprises a RF receiver for receiving the RF signal.

17. System of claim 16, wherein said monitor device comprises a signal processing circuit for processing the RF signal and displaying the processed signal as the blood saturation level of the patient.

18. System of claim 15, wherein said monitor device comprises a multi-functional medical monitor that displays, in addition the blood saturation level, the EKG, pulse and blood pressure of the patient.

19. System of claim 15, wherein said housing comprises two halves biased toward each other, two circuit boards each having mounted thereon one of said processor and transceiver circuits mounted to one of said halves, a switch not responsive to the placement of said finger in said housing provided to said housing to enable manual activation of said radiation emitter, said sensor, and said processor and transmitter circuits.

20. System of claim 15, further comprising:

a power circuit for supplying power to said radiation emitter, said sensor, and said processor and transceiver circuits, said power circuit may be activated or shut down by the activation of a switch located at said housing not responsive to the placement of said finger in said housing or by a signal transmitted from said remote monitor device.

21. An oximeter, comprising:

a housing having an opening through which a finger of a patient is positioned;

a radiation emitter provided in said housing for outputting radiation of multiple frequencies to said finger;

a photo sensor provided in said housing for detecting the radiation passing said finger to acquire data relating to oxygen saturation of blood of the patient;

a processor provided in said housing for calculating from the acquired data the oxygen saturation level of blood of said patient; and a transceiver provided in said housing for establishing a bidirectional telecommunications link between said oximeter and a monitor device at a remote location separate from said oximeter, said transceiver transmitting a RF signal representing the calculated blood saturation level to said monitor device at the remote location.

22. Oximeter of claim 21, wherein said housing includes a display for displaying the calculated blood saturation level of the patient.

23. Oximeter of claim 21, wherein said transceiver comprises a RF transmitter circuit for transmitting said signal via an RF link to a remote RF receiver of a monitor device remote and separate from said oximeter.

24. Oximeter of claim 21, wherein said housing comprises two halves one of which has fitted thereto at least one circuit board whereon at least one of said processor and transceiver is mounted, and a switch not responsive to the placement of said finger in said housing for selectively controlling power to said radiation emitter, photo sensor, processor and transceiver.

25. Oximeter of claim 21, wherein said circuit transceiver can transmit said RF signal at a selectable frequency.

26. Oximeter of claim 21, wherein said RF signal is sent via Bluetooth protocol.

27. An oximeter, comprising:
a housing having an opening through which a finger of a patient is positioned;
a radiation emitter provided in said housing for outputting radiation of multiple frequencies to said finger;
a photo sensor provided in said housing for detecting the radiation passing said finger to acquire data relating to oxygen saturation of blood of the patient;
a processor provided in said housing for calculating from the acquired data the oxygen saturation level of blood of said patient; and
a transmitter provided in said housing for transmitting a RF signal representing the calculated blood saturation level to a remote location;
wherein said processor circuit controls the respective operations of said radiation emitter, said sensor, and said transmitter, said oximeter further comprising a power circuit and a power supply for supplying power to said radiation emitter, said sensor, said transmitter and said processor circuit, the operation of said power circuit may be selectively controlled by a signal transmitted from said monitor device.

28. A system for remotely determining the blood oxygen level in the blood of a patient, comprising:
an oximeter having
a housing with an opening through which a finger of a patient is positioned;
a radiation emitter provided in said housing for radiating said finger with a multi-frequency radiation;
a sensor provided in said housing for acquiring data from the radiation passing said finger;
a processor circuit provided in said housing for operating said radiation emitter and said sensor, and for calculating from the data acquired by said sensor at least the oxygen saturation level of blood of said patient; and
a transmitter circuit provided in said housing for telecommunicatively transmitting the calculated blood saturation level from said housing; and
a monitor device remote from said oximeter having
a receiver circuit for receiving the calculated blood saturation level from said oximeter; and
a display for displaying the received blood saturation level;
wherein said monitor device comprises an activation circuit for controlling the operation of said processor circuit of said oximeter from said monitor device.

* * * * *